United States Patent [19]

Shepherd et al.

[11] Patent Number: 4,970,900

[45] Date of Patent: Nov. 20, 1990

[54] POLE MOUNT ORGANIZER WITH MODULAR INTERCONNECTION RECEPTACLES

[75] Inventors: David J. Shepherd, Laguna Hills; John P. Hall, Santa Ana; Ronald B. Beckman, Mission Viejo, all of Calif.

[73] Assignee: Baxter International, Inc., Deerfield, Ill.

[21] Appl. No.: 304,743

[22] Filed: Jan. 31, 1989

[51] Int. Cl.$^5$ .......................... G01L 7/08; G01L 9/00; G01L 19/14

[52] U.S. Cl. ........................................ 73/756; 73/431; 73/723; 128/675

[58] Field of Search ........................ 73/756, 431, 723; 312/209; 128/675, 672, 673

[56] References Cited

U.S. PATENT DOCUMENTS

| | | | |
|---|---|---|---|
| 4,182,367 | 1/1980 | Day | 73/756 |
| 4,227,420 | 10/1980 | Lamadrid | 128/675 |
| 4,776,343 | 10/1988 | Hubbard et al. | 128/675 |

Primary Examiner—Donald O. Woodiel

Attorney, Agent, or Firm—Debra E. Dahl

[57] ABSTRACT

The present invention provides a modular system for mounting one or more medical devices on an IV pole at a patient's bedside. The system comprises a support plate, and at least one modular interconnection receptacle adapted to be detachably mounted on the support plate and adapted to receive a medical device. In one embodiment, the interconnection receptacle has electrical connection means serving as an electrical conduit between the medical device and a monitor. The means for attaching the medical device to the interconnection receptacle has a greater retention force than the means for attaching the interconnection receptacle to the support plate. Thus, in response to a threshold force on the patient line connected to the medical device, the interconnection receptacle breaks free of the support plate while the medical device remains attached to the interconnection receptacle. This maintains fluid connection to the patient and electrical connection to a monitor in the case of a medical device, such as a pressure transducer.

13 Claims, 6 Drawing Sheets

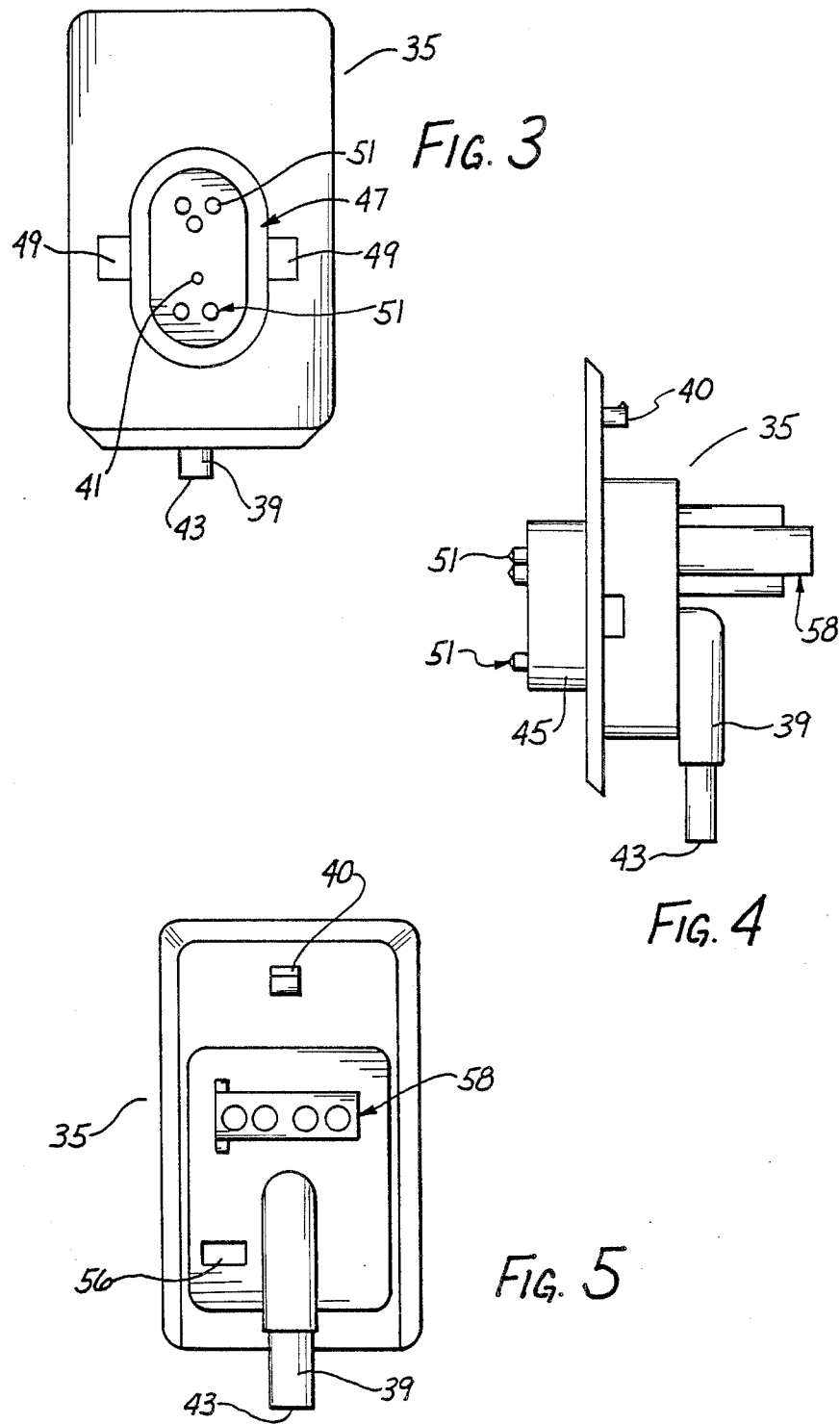

POLE MOUNT ORGANIZER WITH MODULAR INTERCONNECTION RECEPTACLES

FIELD OF INVENTION

The present invention relates to a pole mounted organizer to which various medical devices and accessories can be attached at a patient's bedside. Specifically, the present invention relates to a support plate for mounting on an IV pole with modular interconnection receptacles to which one or more pressure transducers or other medical devices and accessories can be attached, and a pressure transducer for attachment to the modular interconnection receptacles.

BACKGROUND OF THE INVENTION

Invasive blood pressure monitoring is frequently performed on critically infirmed patients in intensive care and critical care units and on patients undergoing critical surgeries. It is gaining widespread acceptance in the care and treatment of cardiac patients as a technique for constant, accurate determination of blood pressure in the heart. The most widely used technique for invasive blood pressure monitoring is catheterization. A catheter is inserted through a peripheral blood vessel into a patient's circulatory system with the distal end of the catheter opening into the blood stream. The catheter is threaded through the blood vessel until it is positioned at the desired location for measuring arterial or venous blood pressure and may be positioned in the right heart or pulmonary artery to measure atrial, ventricular or pulmonary artery pressures.

An IV set is generally attached to the proximal end of the catheter protruding from the patient. An IV solution bag and the IV set assembly contain a solution such as, for example, a sterile saline solution, which flows through the catheter into the patient. The IV solution provides a fluid pathway for monitoring pressure in the patient's circulatory system. By positioning a pressure transducer along the fluid pathway, the blood pressure in the patient's circulatory system can be monitored.

A typical pressure transducer for use in invasive blood pressure monitoring systems comprises a thin diaphragm which is capable of being deflected by the pressure pulses which travel through the fluid column in the catheter and tubing. Some type of mechanism is provided for measuring the deflection of the diaphragm, usually suitable electronic circuitry configured to generate an electrical signal representing the pressure exerted on the diaphragm.

Reusable and disposable pressure transducers are commercially available. Reusable pressure transducers often consist of a disposable dome which functions as a reservoir for the IV fluid. The dome includes a resilient diaphragm contiguous with the diaphragm of the pressure transducer. The pressure pulses are transmitted through the dome diaphragm to the transducer diaphragm. The transducer measures the deflection of the diaphragm and converts the pressure fluctuation into electrical impulses which are transmitted to a monitor. These pressure transducers can be reused following sterilization because the diaphragm of the transducer is not in direct contact with the fluid being administered. Only the disposable dome and diaphragm contact the fluid. An example of a reusable pressure transducer is disclosed and described in U.S. Pat. No. 4,610,256 entitled PRESSURE TRANSDUCER, issued Sept. 9, 1986 in the name of Wallace, the entire disclosure of which is incorporated herein by reference.

Disposable pressure transducers generally include a housing defining a flow-through chamber having an inlet and outlet port, and a pressure transducer mounted in a second chamber. The transducer is exposed to the first chamber but separated from the fluid in the first chamber by an insulating medium, such as silicone gel. Fluid pressure can be transmitted across the insulating medium, but electrical current cannot.

The transducer is generally a silicon chip a portion of which forms a thin diaphragm which deflects in response to pressure impulses in the fluid column. Electrical conductors in contact with circuitry on the silicon chip lead from the transducer and are encased in an insulated sheath to form a short length of electrical cable with an end connector (a "pigtail" or "adapter" cable). The adapter cable can in turn be connected to a longer extension cable leading to a monitor.

Examples of disposable pressure transducers are described and disclosed in U.S. Pat. No. 4,539,998 entitled PRESSURE TRANSDUCER ASSEMBLY, issued Sept. 10, 1985 in the name of McCord, U.S. Design Pat. No. 282,284 entitled TRANSDUCER HOUSING ASSEMBLY FOR MONITORING BLOOD PRESSURE AND THE LIKE, issued Jan. 21, 1986, in the name of McCord et al, and U.S. Pat. No. 4,576,181 entitled A DISPOSABLE PRESSURE TRANSDUCER APPARATUS FOR MEDICAL USE, issued Mar. 18, 1986 in the name of Wallace et al. the disclosures of which are incorporated herein by reference.

Typically, the pressure transducers have mounting brackets as shown on the transducers in FIG. 1 of U.S. Pat. No. 4,576,181, FIG. 1 of U.S. Pat. No. 4,539,998, and FIG. 1 of U.S. Design Pat. No. 282,284. The brackets may have slots formed therein through which tape or straps may be positioned to secure the transducer to an IV pole, to the patient himself, or to a fluid manifold adjacent the patient's bedside.

Another example of a disposable pressure transducer is shown in U.S. Pat. No. 4,776,343 entitled DISPOSABLE PRESSURE TRANSDUCER FOR USE WITH A CATHETER, issued in the name of Hubbard et al. The housing of the Hubbard pressure transducer has a flange for horizontal or vertical mounting on a conventional pole clamp on an IV pole, and a splash curtain to protect the cable connection from fluid splash.

FIG. 1 herein shows a prior art medical device organizer mounted on an IV pole with transducers of the type disclosed in U.S. Pat. Nos. 4,576,181 and 4,539,998 attached. As shown in FIG. 1, the mounting brackets of transducer 1 (the type disclosed in the '181 patent) slide into the slots or grooves provided on the organizer by flanges 3, whereas the mounting brackets of transducer 5 (the type disclosed in the '998 patent) slide into the slots or grooves provided on the organizer by flanges 7.

Short lengths of electrical cable ("pigtail" or "adapter" cables) 9 and 11 extend from each transducer to electrical connectors 13 and 15, respectively. Electrical connectors 13 and 15 are in turn connected to electrical connectors 17 and 19 on electrical cables 21 and 23, respectively, which lead to a monitor. Port 14 formed in electrical connector 13 provides means for venting and calibrating the back side of pressure transducer 1 through an air passageway in adapter cable 9. Tubing 25 and 27 connect to an IV bag and tubing 29 and 31 connect to a catheter inserted into the patient.

The organizer shown in FIG. 1 is a convenient method of mounting several pressure transducers or other medical devices and accessories, such as, for example, flush devices, stopcocks, and tubing in a neat organized fashion on an IV pole at a patient's bedside. One of the disadvantages of the support plate shown in FIG. 1 is that in response to patient strain on lines 29 and 31, there is danger of breaking the connection between the tubing and the pressure transducer at stopcocks 2B and 30, respectively, which interrupts fluid flow to the patient and can pose a serious threat to the patient. Another disadvantage is that the organizer provides no electrical interconnection between the pressure transducer or other medical device and a monitor. Thus, it is necessary to provide an adapter cable as part of the transducer or medical device.

There is a need for a pole mounted organizer that neatly and conveniently holds a plurality of medical devices, but at the same time provides some strain relief if patient movement exerts too much force on the tubing connected to the medical device. There is also a need for an organizer that provides means for connecting a medical device to a monitor without incorporating an adapter cable into the medical device.

SUMMARY AND OBJECTS OF THE INVENTION

It is therefore an object of the present invention to provide a pole mounted organizer for pressure transducers and other medical devices with modular interconnection receptacles that break away from a support plate in response to a threshold force on the line leading to the patient.

Another object of the present invention is to provide modular interconnection receptacles for connecting pressure transducers and other medical devices to the organizer.

It is also an object of the present invention to provide electrical connection means on the interconnection receptacles for connecting transducers and other devices to monitors without the need for adapter cables.

The present invention is directed to a modular system for mounting one or more medical devices, with or without electrical connection, on an IV pole or other support structure at the patient's bedside. The system comprises a support plate or member and at least one modular interconnection receptacle adapted to be detachably mounted on the support plate and adapted to receive a medical device, such as, for example, a pressure transducer. The modular interconnection receptacle has connection means for securely holding the medical device when the device is attached to it.

The modular interconnection receptacle also has means for detaching from the support plate in response to a pulling force on the patient line attached to the medical device. The retention force between the medical device and the interconnection receptacle is greater than the retention force between the interconnection receptacle and the support. This enables the modular interconnection receptacle to break away from the support plate while at the same time maintaining the fluid connection between the device and the patient, and the electrical connection between the device and the monitor.

For mounting medical devices that require electrical connection to a monitor, the modular interconnection receptacle has electrical connection means that makes electrical contact with the medical device. Electrical signals can then be transmitted to a monitor through a standard extension cable connected to the back side of the interconnection receptacle. Incorporating electrical connection means into the interconnection receptacle eliminates the need for providing the transducer or medical device with an adapter cable.

The present invention is also directed to a pressure transducer designed to mate with the modular interconnection receptacle. The pressure transducer has means for attaching to and detaching from the interconnection receptacle. The transducer is vented to atmosphere on the back side of the diaphragm through the interconnection receptacle. Preferably, the means for attaching the transducer creates a sealed chamber to permit calibration of the pressure transducer through the vent by applying a pressure, preferably a negative pressure or vacuum, to the inside of the sealed chamber. Electrical connection means provided on the pressure transducer is adapted to mate with the electrical connection means on the interconnection receptacle.

Preferably, the pressure transducer or other medical device is attached to the interconnection receptacle by means of tabs that mate with tabs on or slots in the interconnection receptacle. The tabs on the transducer or medical device are preferably adapted for one hand manipulation. In a preferred embodiment, the system has a protective cover pivotally mounted on the support plate which is retractable to expose the interconnection receptacles. In the open position, the cover provides a hood protecting the back side cable connections to the interconnection receptacles from fluid splash. In the closed position, the protective cover shields the exposed electrical connectors on the interconnection receptacles.

These and other objects and features of the present invention will become more fully apparent from the following detailed description and the claims taken in conjunction with the accompanying drawings.

BRIEF DESCRIPTION OF THE DRAWINGS

FIG. 3 is a front view of a preferred embodiment of the modular interconnection receptacle.

FIG. 4 is a side view of a preferred embodiment of the modular interconnection receptacle.

FIG. 5 is a rear view of a preferred embodiment of the modular interconnection receptacle.

DETAILED DESCRIPTION OF THE PREFERRED EMBODIMENT

It will be readily appreciated that the components of the present invention, as generally described and illustrated in the figures herein, could be arranged and designed in a wide variety of different configurations. The following detailed description of a preferred embodiment of the organizer or system of the present invention, as represented in FIGS. 1–12, is not intended to limit the scope of the invention as claimed but is merely representative of one presently preferred embodiment of the invention.

Figure 2:
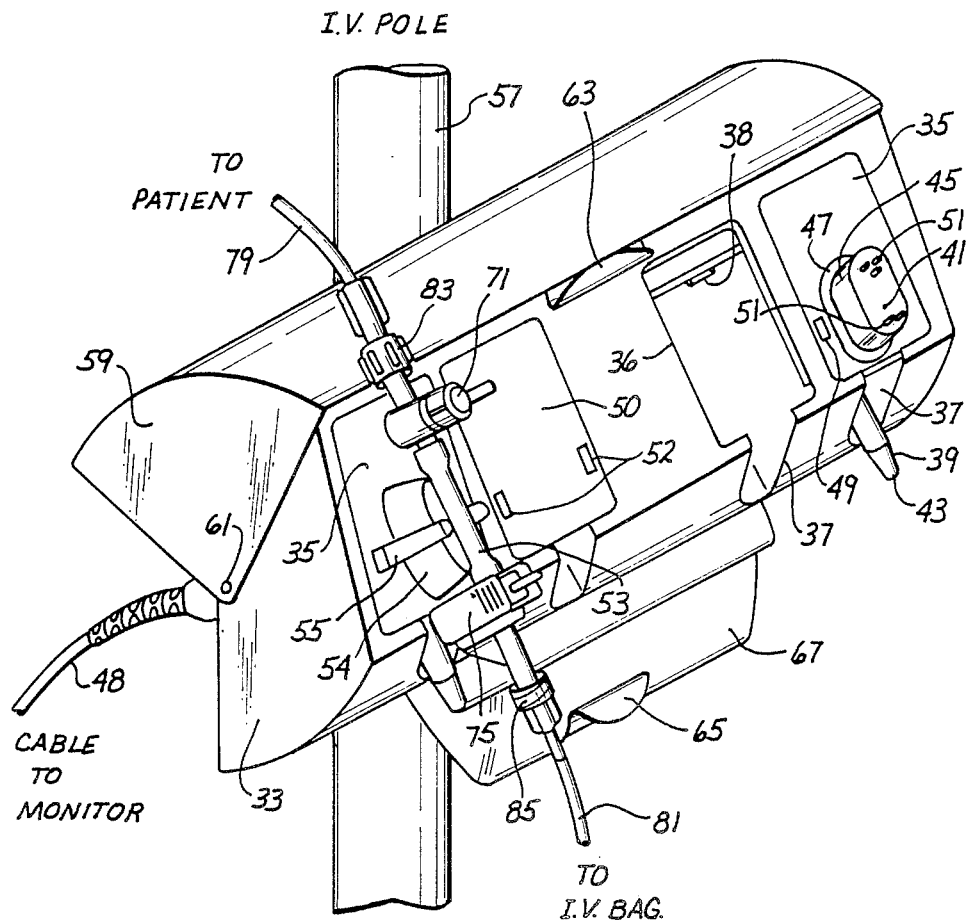
FIG. 2 is a perspective view of a preferred embodiment of the organizer of the present invention showing the modular interconnection receptacles with and without electrical connection means and a transducer mounted on one of the interconnection receptacles.

Referring first to FIG. 2, there is shown a support member 33 designed to hold from one to four modular interconnection receptacles 35. Support member 33 is preferably provided with one to four cut out holes 36 corresponding to the outer dimension of the interconnection receptacles 35 with a lower portion 37 of the hole opening below the interconnection receptacle. In other embodiments, the support member could be designed to hold more than four interconnection receptacles.

Tube 39 attached to the back of interconnection receptacle 35 or integral with it projects downwardly through opening 37 in the support member. Port 41 formed in interconnection receptacle 35 communicates with tube 39 and opening 43 in tube 39 to provide an air passageway through which a pressure transducer or other device can be vented to atmosphere when attached to the interconnection receptacle.

Means for detachably mounting the interconnection receptacle on the support member is provided across the back of the cut out hole 36 and preferably comprises a flexible tab 38 that mates with a corresponding tab 40 on the back side of the interconnection receptacle as shown in FIGS. 4 and 5.

Means for attaching the medical device to the interconnection receptacle preferably comprises a slot formed in the interconnection receptacle or a flexible tab adapted to receive or mate with a flexible tab projecting from the medical device. Preferably, a pair of slots 49 are provided on interconnection receptacle 35 for engagement by a pair of tabs 55 projecting from the medical device. Preferably, the tabs on the medical device can be manipulated with one hand to attach or detach the medical device.

The retention force between the tabs of the medical device and the slots of the interconnection receptacle should be greater than the retention force between tab 38 on the support member and tab 40 on the interconnection receptacle. This ensures that the medical device or pressure transducer which is connected to the patient through IV tubing will not break away from the interconnection receptacle in response to a force on the patient line. Instead, the interconnection receptacle breaks away from the support member ensuring that the fluid connection to the patient remains intact and also that electrical continuity is maintained.

Figure 1:
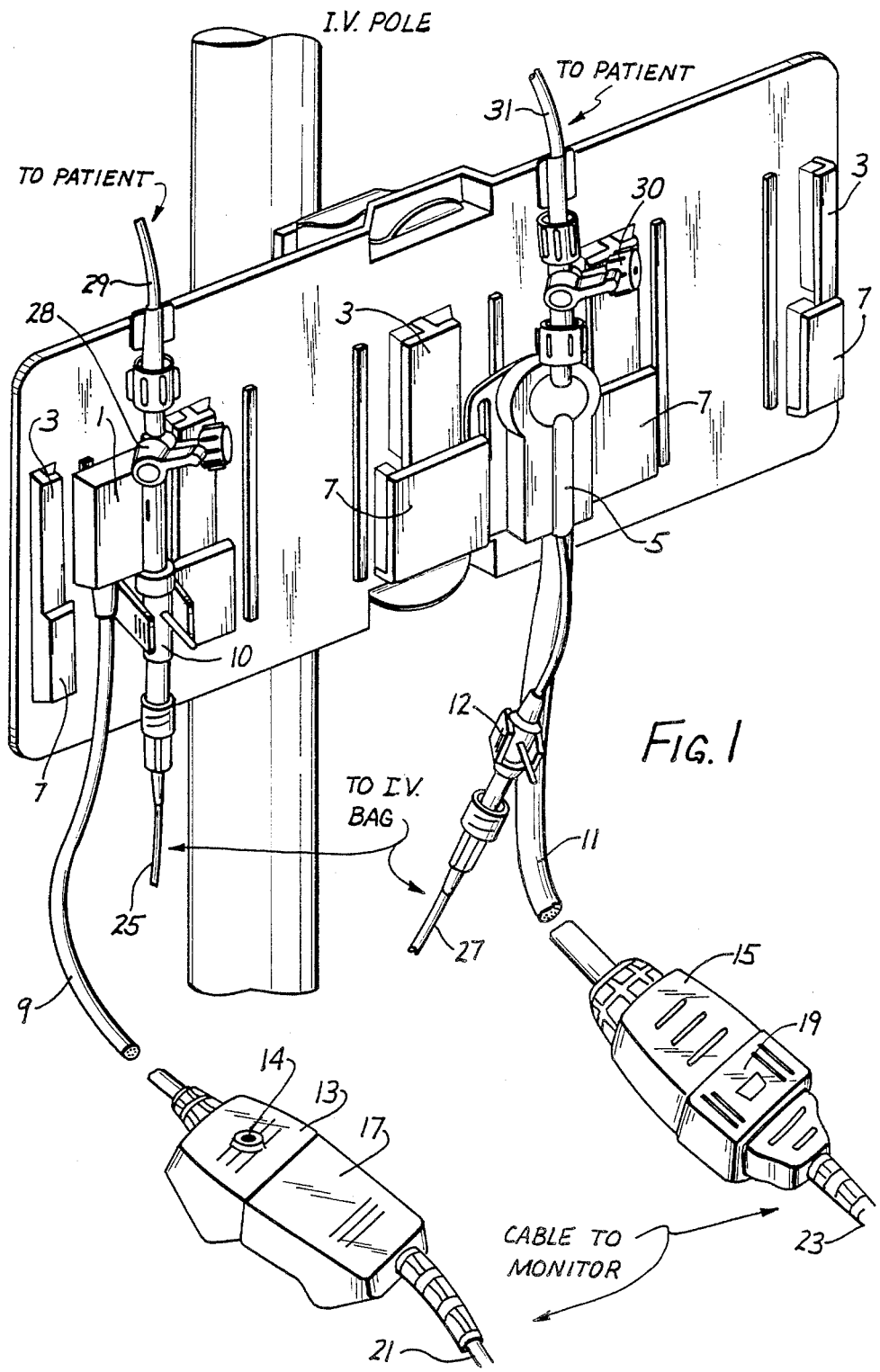
FIG. 1 is a perspective view of a conventional pole mounted organizer with pressure transducers mounted on it.

This breakaway connection is an important feature of the present invention. The prior art method of mounting transducers on a support plate on an IV pole as shown in FIG. 1 had problems with breakage of the fluid flow connection at stopcock 2B in response to a pulling force on the patient line exceeding a certain threshold. This could be life threatening to the patient because with no back pressure from the IV source, the patient could bleed to death at the catheter insertion site, or the open fluid path could become contaminated with bacteria.

Another problem with strain on the patient line is that the catheter positioned in the vessel of the patient may pull out of the patient in response to patient movement or strain. This could cause the patient to bleed to death if the situation goes undetected. The breakaway feature of the present invention also solves this problem by providing catheter pull-out strain relief.

For those devices such as a pressure transducer that require electrical connection to a monitor, modular interconnection receptacle 35 is provided with projection 45 having electrical contact means 51. FIGS. 3, 4, and 5 show the front, side, and rear view of the interconnection receptacle with electrical connection means. In this embodiment, the electrical contact means comprise five electrical spring pins or pogo pins which in turn make electrical contact with the medical device, in this case a pressure transducer. Preferably, spring pins 51 are in contact with solder pads on a ceramic circuit board on the back side of the pressure transducer.

The electrical contact means on the interconnection receptacle could also be a circuit board with pins, a circuit board, a circuit board with sockets or contacts, or pins with fork contacts. The mating electrical connection on the transducer could also be sockets, spring contacts, pins or blades. Incorporating modular electrical connection means into the interconnection receptacle eliminates the need for incorporating an adapter cable into the medical device or pressure transducer. This significantly reduces the cost of a disposable pressure transducer.

Projection 45 is surrounded by sealing means, preferably a rubber gasket or O-ring 47. O-ring 47 ensures that when the pressure transducer assembly 53 is attached to interconnection receptacle 35 and in electrical contact with pins 51, an air-tight space is created within shroud 54 of the pressure transducer assembly. This air space vents to atmosphere through port 41 in projection 45 and through tube 39. The O-ring sealing means creates an air-tight space permitting back side calibration of the pressure transducer by applying a pressure at opening 43, preferably a negative pressure or vacuum as disclosed in U.S. Pat. No. 4,610,256 in the name of Wallace.

The back side of interconnection receptacle 35 shown in FIG. 5 provides means for electrically connecting the interconnection receptacle to extension cables which currently exist in hospitals. In a preferred embodiment, electrical contact means comprising four sockets 58 are provided on the back side of receptacle 35. The sockets make the interconnection receptacle compatible with most standard electrical cables utilized by hospitals to connect medical devices to monitors. In lieu of sockets, a circuit board or electrical pins can be provided on the back side of the receptacle. Electrical cable 48 shown in FIG. 2 is attached to the electrical connection means on the back side of the receptacle. Cable 4B is then connected to a monitor (not shown) making the electrical connection between the pressure transducer or other medical device and the monitor complete.

In one preferred embodiment of the electrical connection means, four spring pins 51 are directly wired to four sockets 5B. This wiring provides monitor recognition of the attachment or detachment of the pressure transducer for most types of monitors. In another preferred embodiment, in addition to the four directly wired pins to sockets, a fifth spring pin is wired to one of the excitation sockets via a shunt resistor which connects the negative excitation of the pressure transducer to the positive excitation from the monitor, or vice versa. This wiring allows for monitor recognition of the attachment or detachment of the pressure transducer in other types of monitors. A preferred shunt resistor provides resistance in the range of 425 to 800 ohms, one-eighth watt. The most preferred resistance is 590 ohms±1%, one-eighth watt.

Preferably, the interconnection receptacle provides a ring 56 on the back side, shown in FIG. 5, to attach a tie wrap to extension cable 48 to discourage loss of electrical connection with interconnection receptacle 35 if the receptacle becomes disconnected from the support member.

The interconnection receptacle can be provided with or without electrical connection means. Some medical devices to be attached to support member 33, such as for example, flush devices, tubing, and stopcocks, do not require electrical connection to a monitor. In these cases, a non-electrical version 50 of the interconnection receptacle is provided. The non-electrical version preferably presents a flat surface without projection 45 and without sealing means 47. Attachment means are provided on the flat surface, such as slots 52, or tabs which mate with tabs or slots on the non-electrical medical device. Alternately, some type of clamp means can be provided on interconnection receptacle 50 to hold the non-electrical medical device.

In a preferred embodiment, support member 33 is designed to be mounted on IV pole 57 as shown in FIG. 2, and preferably has flanges for attachment to existing IV pole clamps. FIG. 2 shows tabs 63 and 65 projecting from a standard IV pole clamp (not shown) engaging an upper flange (not shown) and a lower flange 67 of the organizer. The support member could also be mounted at the patient's bedside on any type of support structure. The support member is preferably mountable at an angle 0°, 15°, 90°, or anywhere in the 15° to 90° range, from the vertical axis of the IV pole. In FIG. 2, the organizer is mounted at a 15° angle from the vertical axis. Mounting the organizer at a 15° to 90° angle from the vertical axis provides improved transducer fluid path visibility for detecting bubbles.

In a preferred embodiment, support member 33 has a protective shield or cover 59 that is pivotally mounted on the support member on protruding posts 61. Shield 59 is pivotal to a closed position to cover the interconnection receptacles mounted on the support member and to prevent accidental contact with electrical pins 51. Shield 59 is retractable to expose the interconnection receptacles and in the retracted position protects the cable connections on the back side of the interconnection receptacles from fluid splash.

In a preferred embodiment of the pole mount organizer of the present invention as shown in FIG. 2, support member 33 and shield 59 are designed with minimal surfaces and maximum curved surfaces for ease of cleaning. Shield 59 and modular interconnection receptacles 35 and 50 have the additional advantage of easy removal for cleaning or replacement.

The system of the present invention includes a pressure transducer specifically designed with modular connection means for mating with modular interconnection receptacle 35. In a preferred embodiment, the pressure transducer is of the same general type disclosed in U.S. Pat. No. 4,576,181 in the name of Wallace et al. However, the structure of the pressure transducer assembly and housing is substantially different.

Figure 6:
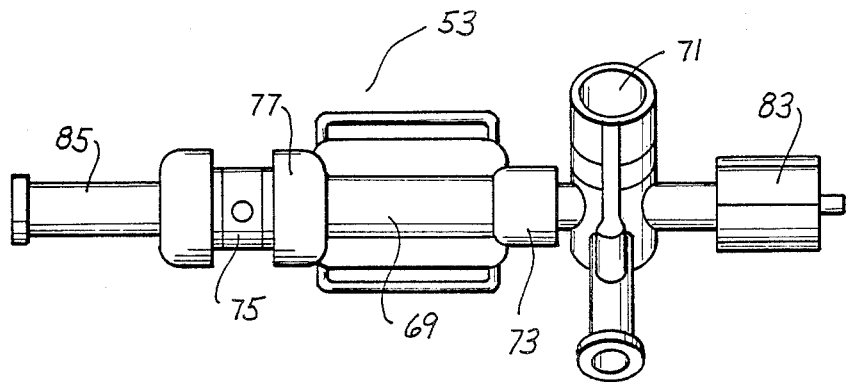
FIG. 6 is a top view of a preferred embodiment of the pressure transducer of the present invention with a stopcock and flush device attached.
Figure 7:
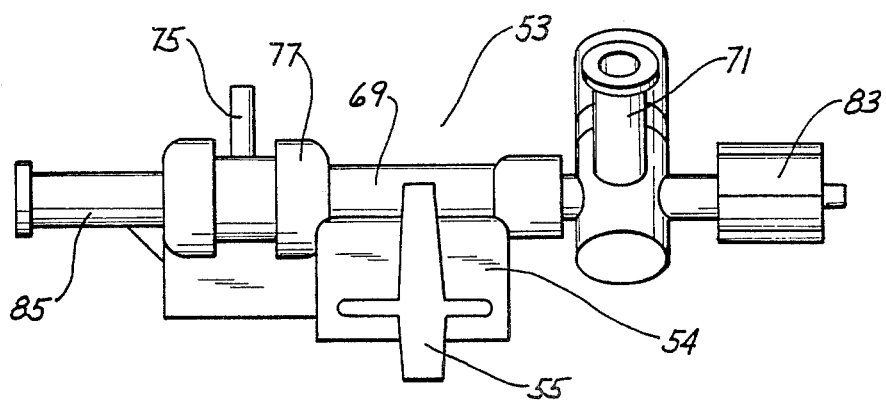
FIG. 7 is a side view of the pressure transducer shown in FIG. 6.
Figure 8:
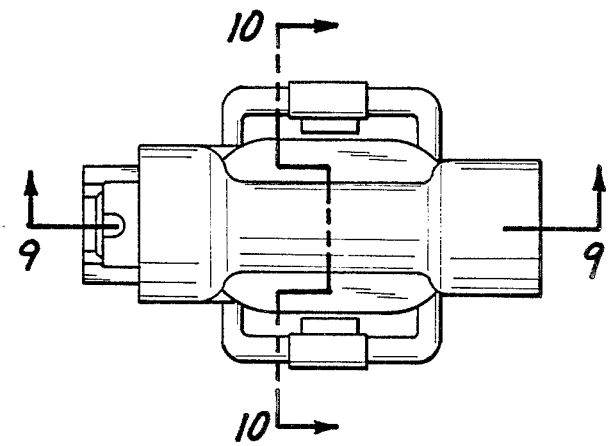
FIG. 8 is a top view of a preferred embodiment of the pressure transducer of the present invention without the stopcock or flush device attached.

The pressure transducer of the present invention as shown in FIGS. 6-12 has a flow-through chamber 69 which is connected at one end to stopcock 71 by luer lock connector 73 (FIGS. 6 and 7) and is connected at the other end to flush valve 75 by luer lock connector 77 (FIGS. 6 and 7). The stopcock 71 is in turn connected to tubing 79 leading to the patient as shown in FIG. 2. Flush device or valve 75 is in turn connected to tubing 81 leading to an IV source as shown in FIG. 2. The tubing 79 and 81 is connected to the stopcock and flush device, respectively, by luer lock connectors 83 and 85, respectively.

The patient line 79 is connected to a catheter which is inserted into the patient's blood vessel. The continuous fluid column needed to sense the patient's blood pressure is provided by flowing IV solution from the IV source through line B1, pressure transducer 53, and through tubing 79 into the patient's blood stream. As the patient's heart pumps blood, periodic pressure pulses are transmitted through the patient's blood vessels and along the fluid column to pressure transducer 53.

Figure 9:
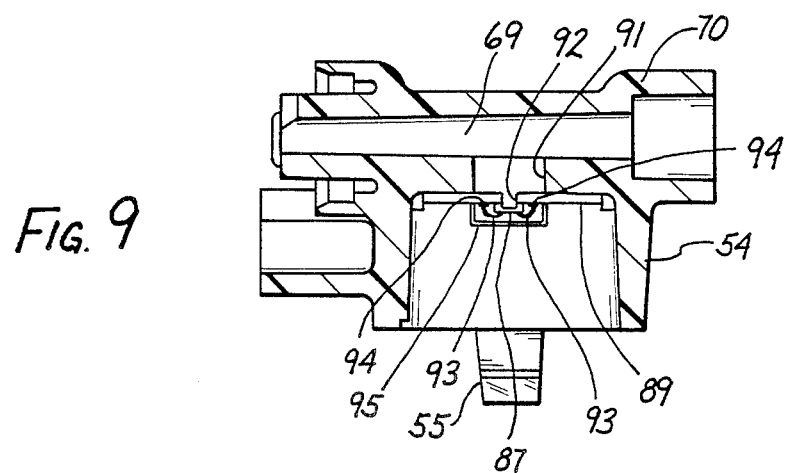
FIG. 9 is a cross-sectional view of the pressure transducer taken along line 9—9 of FIG. 8.
Figure 10:
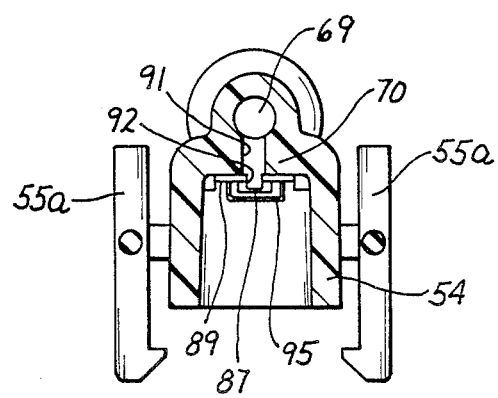
FIG. 10 is a cross-sectional view of the pressure transducer taken along line 10—10 of FIG. 8.
Figure 11:
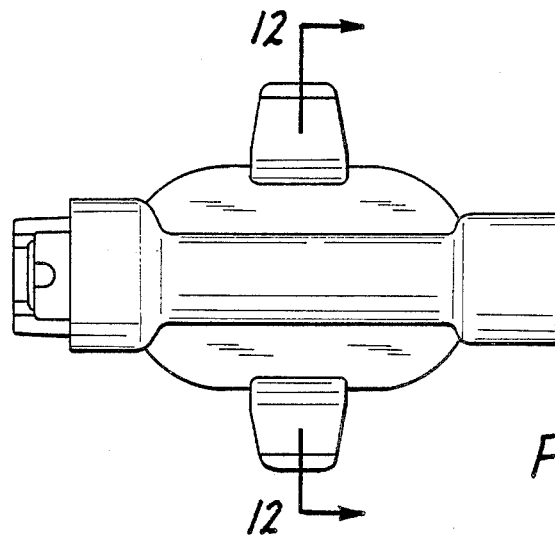
FIG. 11 is a top view of another preferred embodiment of the pressure transducer of the present invention without the stopcock and flush device attached.
Figure 12:
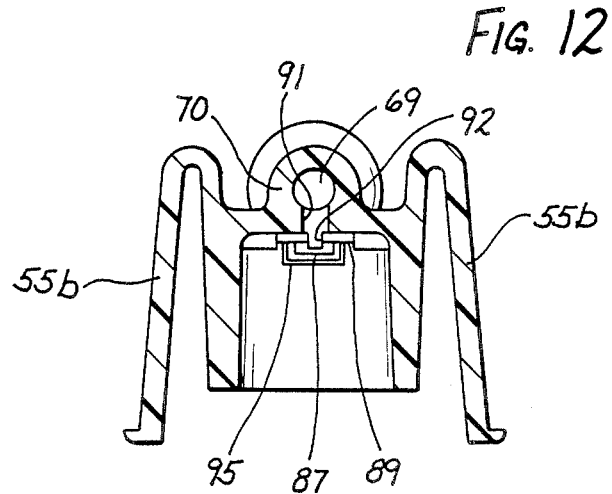
FIG. 12 is a cross-sectional view of the pressure transducer taken along line 12—12 of FIG. 11.

A cross-sectional view of transducer 53 along the longitudinal axis (line 9—9 of FIG. 8) of the flow-through chamber is shown in FIG. 9. Cross-sectional views perpendicular to the longitudinal axis of the flow-through chamber are shown in FIGS. 10 and 12. FIG. 10 is taken from line 10—10 of FIG. 8. FIG. 12 is taken from line 12—12 of FIG. 11.

Referring to FIGS. 9, 10, and 12 the pressure transducer has four resistive elements ion-implanted on a silicon chip to form a conventional Wheatstone bridge. A central portion of the chip is etched away by chemical etching techniques to form a piezoresistive diaphragm 87. The pressure pulses in chamber 69 are transmitted to diaphragm 87.

The silicon chip is mounted on a dialectric substrate such as a ceramic circuit board 89. A hole 91 formed in the housing of the flow-through chamber communicates with hole 92 formed in substrate 89. Hole 91 is filled with an insulating medium, preferably silicone gel, through which pressure pulses can be transmitted but which isolates the electrical components of the pressure transducer from the patient.

The diaphragm is electrically connected to the substrate by wires 93 leading from the diaphragm to solder pads 94 on the substrate as disclosed in U.S. Pat. No. 4,576,181. An opaque cap is placed over the diaphragm and wires to protect them from mechanical injury and exposure to light. Electrical pins 51 of the interconnection receptacle in turn contact solder pads 94 establishing the electrical connection between the transducer and the interconnection receptacle when the transducer assembly is snapped into place on the interconnection receptacle.

The housing 70 forming the flow-through chamber includes a shroud 54 which covers the pressure transducer and extends beyond the transducer. The shroud has tab members 55 or other means for attaching the shroud portion of the transducer assembly to the interconnection receptacle.

FIG. 10 shows bar-shaped flexible tabs 55a on shroud 54 that mate with slots 49 on interconnection receptacle 35. FIG. 12 shows U-shaped flexible tab members 55b on shroud 54 that mate with slots 49 in the interconnection receptacle. Either tab arrangement is designed to be easily manipulated with one hand to attach and detach the transducer from the interconnection receptacle. Similar tab like arrangements can be included on other non-electrical devices such as flush devices, stopcocks, and tubing in order to mount those devices on the non-electrical version 50 of the interconnection receptacle.

The invention may be embodied in other specific forms without departing from its spirit or essential characteristics. The described embodiments are to be considered in all respects only as illustrative and not restrictive. The scope of the invention is therefore indicated by the appended claims, rather than by the foregoing description. All changes which come within the meaning and range of the equivalency of the claims are to be embraced within their scope.

What is claimed is:

1. A system for holding one or more medical devices, comprising:
   (a) a support;
   (b) at least one modular interconnection receptacle adapted to be detachably mounted on the support and adapted to receive the medical device;
   (c) the modular interconnection receptacle having attachment means for receiving and holding the medical device and means for detaching from the support in response to a threshold force on the medical device, the force required to break the attachment between the medical device and the interconnection receptacle being greater than the force required to detach the interconnection receptacle from the support.

2. A system for mounting one or more medical devices near a patient, comprising:
   (a) a support;
   (b) at least one modular interconnection receptacle adapted to be detachably mounted on the support and adapted to receive the medical device;
   (c) the modular interconnection receptacle having attachment means for receiving and holding the medical device and means for detaching from the support in response to a threshold pulling force on a line connecting the medical device to the patient, the attachment means having a retention force greater than the retention force of the detachment means;
   (d) the interconnection receptacle having electrical connection means serving as an electrical conduit between the pressure transducer and a pressure monitor.

3. A system according to claim 2, wherein said electrical connection means comprises first electrical contact means for making electrical connection with the medical device and second electrical contact means for connecting an electrical cable leading to the monitor.

4. A system according to claim 3, wherein wiring from the first electrical contact means to the second electrical contact means includes a shunt resistor connecting positive excitation to negative excitation, the electrical connection means between the medical device and the interconnection receptacle thereby providing monitor recognition of the medical device when the interconnection receptacle is connected to the electrical cable leading to the monitor.

5. A system according to claim 5, wherein the first electrical contact means comprises spring pins which contact a ceramic circuit board on the medical device.

6. A system according to claim 2, wherein the medical device is a pressure transducer, the attachment means has sealing means to provide an airtight seal between the pressure transducer and the interconnection receptacle when the pressure transducer is attached, and the interconnection receptacle has a port formed therein communicating with the pressure transducer to vent the pressure transducer to atmospheric pressure and for use in calibrating the pressure transducer.

7. A system according to claim 1 or 2, wherein the support has a cut out hole with a dimension corresponding to the outer dimension of the interconnection receptacle and a tab extending into the hole for mating with a tab on the interconnection receptacle for detachably mounting the interconnection receptacle on the support.

8. A system according to claim 1 or 2, wherein the support is provided with more than one cut out hole for connecting more than one modular interconnection means.

9. A system according to claim 1 or 2, wherein the interconnection receptacle has slots formed therein which mate to tabs on the medical device, the tabs on the medical device adapted for one hand manipulation to attach and detach the medical device from the interconnection receptacle.

10. A system according to claim 1 or 2, wherein the support has a protective cover pivotally mounted on the support, the cover being pivotal to a closed position to cover the interconnection receptacle and to an open position to expose the interconnection receptacle, the cover providing a hood to protect back side cable connections to the interconnection receptacle from fluid splash when the cover is in the open position.

11. A pressure transducer assembly for monitoring pressure in a fluid, comprising:
   (a) a housing comprising a flow-through fluid chamber with inlet and outlet ports and an open chamber covered by a shroud;
   (b) a pressure transducer means mounted in the open chamber having a diaphragm coupled to the flow-through chamber for sensing fluid pressure pulses within a fluid in the flow-through chamber and having means for converting the sensed pressure pulses into electrical signals;
   (c) attachment means on the housing adapted to attach the housing to an interconnection receptacle to create a closed chamber within the shroud upon attachment and wherein upon attachment the pressure transducer is electrically coupled to electrical connection means on the interconnection receptacle, the interconnection receptacle being adapted to serve as an electrical conduit between the pressure transducer means and a pressure monitor.

12. A pressure transducer assembly according to claim 11, wherein the attachment means comprises tabs that mate with slots or tabs on the interconnection receptacle, wherein the tabs are adapted for one hand manipulation to attach and detach the assembly from the interconnection receptacle.

13. A pressure transducer assembly according to claim 11, wherein the pressure transducer means vents to the inside of the shroud and the shroud when couple to the interconnection receptacle forms an airtight chamber with the interconnection receptacle providing a vent to atmospheric pressure and means for calibrating the pressure transducer by applying a pressure to the inside of the shroud covered chamber.

* * * * *